United States Patent [19]

Kaplitt

[11] Patent Number: 6,040,172
[45] Date of Patent: Mar. 21, 2000

[54] DEFECTIVE DNA VIRAL VECTOR COMPRISING A NEURAL TISSUE-SPECIFIC PROMOTER FOR IN VIVO EXPRESSION OF A GENE

[75] Inventor: Michael G. Kaplitt, New York, N.Y.

[73] Assignee: The Rockefeller University, New York, N.Y.

[21] Appl. No.: 08/381,924

[22] PCT Filed: Aug. 16, 1993

[86] PCT No.: PCT/US93/07685

§ 371 Date: Feb. 14, 1995

§ 102(e) Date: Feb. 14, 1995

[87] PCT Pub. No.: WO94/04695

PCT Pub. Date: Mar. 3, 1994

Related U.S. Application Data

[63] Continuation-in-part of application No. 07/930,875, Aug. 14, 1992, abandoned.

[51] Int. Cl.[7] ............................ C12N 15/63; C12N 15/00; C12N 15/09; C12N 5/00
[52] U.S. Cl. ..................... 435/320.1; 435/455; 435/456; 435/457; 435/69.1; 435/69.8; 435/325; 424/93.21; 514/44; 800/9
[58] Field of Search ..................................... 514/44; 800/2, 800/9; 435/320.1, 172.3, 69.1, 69.8, 325, 455, 456, 457; 424/93.21

[56] References Cited

U.S. PATENT DOCUMENTS

| | | | |
|---|---|---|---|
| 4,546,082 | 10/1985 | Kurjan et al. | 435/172.3 |
| 5,288,641 | 2/1994 | Roizman | 435/320.1 |

FOREIGN PATENT DOCUMENTS

| | | |
|---|---|---|
| 0 116 201 | 8/1984 | European Pat. Off. . |
| 0 301 669 | 2/1989 | European Pat. Off. . |
| WO 92/07945 | 5/1992 | WIPO . |
| WO 94/04695 | 3/1994 | WIPO . |

OTHER PUBLICATIONS

Andersen et al., Society for Neuroscience Abstracts, vol. 17, Abstract No. 570.6, 1991.
Kaplitt et al., Neurobiology, vol. 91, pp. 8979–8983, Sep. 1994.
Eck & Wilson, 'Gene–Based Therapy' in Goodman & Gilman's The Pharmacological Basis of Therapeutics, McGraw–Hill: New York, pp. 77–101, 1995.
Houdebine, Journal of Biotechnology, vol. 34, pp. 269–287, 1994.
Eliot Marshal. Gene Therapy's Growing Pains. Science. vol. 269 (1995) p1050–1055, Aug. 25, 1995.
Clague P. Hodgson. Advances in Vector Systems For Gene Therapy. Exp. Opin. Ther. Patents (1995) 5 (5) p. 459–460.
Fred D. Ledley. Clinical Considerations in the Design of Protocols for Somatic Gene Therapy. Human Gene Therapy 2:77–83 (1991).
Orkin, S.H.; Motulsky, A.G. Report and Recomendations of the Panel to Assess the NIH Investment in Research on Gene Therapy. NIH Dec. 7, 1995.
Hatsoglou et al. The Journal of Biological Chemistry. vol. 265 No. 28 pp. 17285–17293, Oct. 5, 1990.
Donovan et al., 1992, Proc. Natl. Acad. Sci. USA89:2345–49.
Federoff et al., 1992, Proc. Natl. Acad. Sci. USA 89 1636–40.
Fink et al., 1992, Human Gene Ther. 3:11–19.
Huang et al., 1992, Exp. Neurol. 115:303–16.
Johnson et al., 1992, Mol. Brain Res. 12:95–102.
Kaplitt et al., 1992, Neurosci. Abstracts 10:500 & 22nd Annual Meeting of the Society for Neuroscience, Anaheim, USA, Oct. 25–30, 1992.
Miyanohara et al., 1992, New Biol. 4:238–46.
Neve et al., 1992, Mol. Neurobiology 5:131–41.
Breakefield et al., 1991, New Biol. 3:203–218.
Kaplitt et al., 1991, Mol. Cell. Neurosci. 2:320–330.
Geller, 1991, J. Vir. Meth. 31:229–38.
Geller, 1991, J. Neuroscience Meth. 36:91–103.
Geller et al., 1991, TINS 14:428–32.
Kaplitt et al., 1991, Soc. Neurosci. Abs. 17:1285 (No.513.3).
Mellencamp et al., 1991, Clin Res. 39:705a.
Chiocca et al., 1990, New Biol. 2:739–746.
Dobson et al., 1990, Neuron 5:353–360.
Freese et al., 1990, Biochem. Pharmacol. 40:2189–99.
Geller et al., 1990, Proc. Natl. Acad. Sci. USA 87:8950–54.
Geller et al., 1990, Proc. Natl. Acad. Sci. USA 87:1149–53.
Boothman et al., 1989, FEBS Letts. 258:159–62.
Coen et al., 1989, Proc. Natl. Acad. Sci USA 86:4736–40.
Geller et al., 1988, Science 241:1667–1669.
Ho et al., 1988, Virology 167:279–83.
Kwong et al., 1985, Virology 142:421–25.
Kwong et al., 1984, J. Virol. 51:595–603.
Frenkl et al., 1982, Eukaryotic Viral Vectors, Gluman, ed., Cold Spring Harbor Lab., pp. 205–9.
Spaete et al., 1982, Cell 30:295–304.

Primary Examiner—Bruce R. Campell
Assistant Examiner—Jill D. Martin
Attorney, Agent, or Firm—Klauber & Jackson

[57] ABSTRACT

A replication defective DNA viral vector that comprises a gene of interest encoding a protein having a demonstrated therapeutic effect on a host cell is disclosed. The vector comprises the gene in operable linkage with a neural tissue-specific promoter, which is a promoter derived from a gene normally produced in the host cell. In particular an HSV-1 vector is used. A preferred DNA defective vector is the dvHBENK which includes a promoter prepared from the rat preproenkephalin gene, the promoter being in operable linkage with the lacZ gene. The disclosed DNA viral vector is useful for achieving stable in vivo long-term expression, in particular in mammalian brain cells.

21 Claims, 5 Drawing Sheets

FIG. 3A
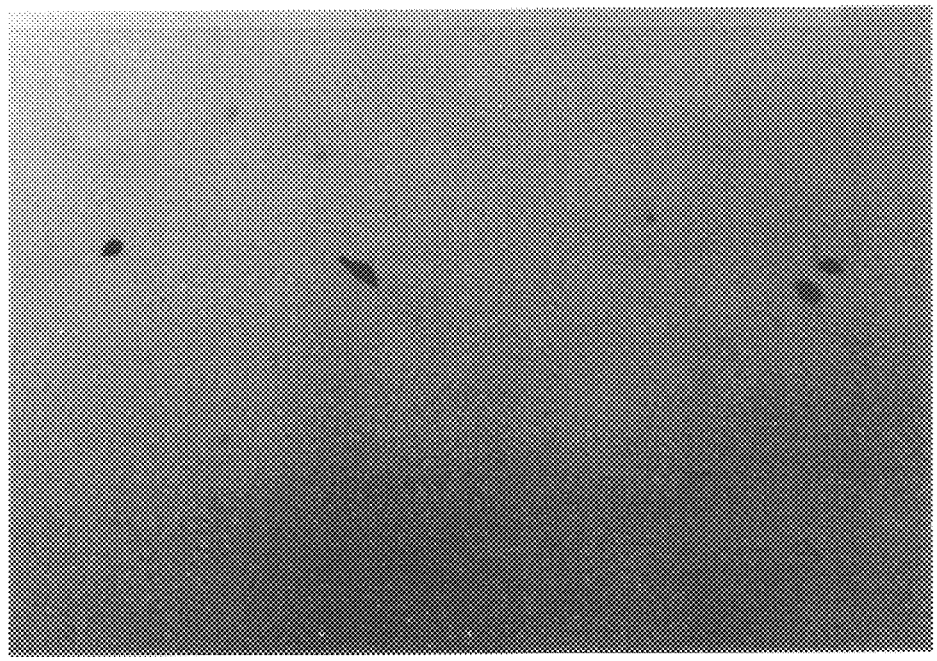
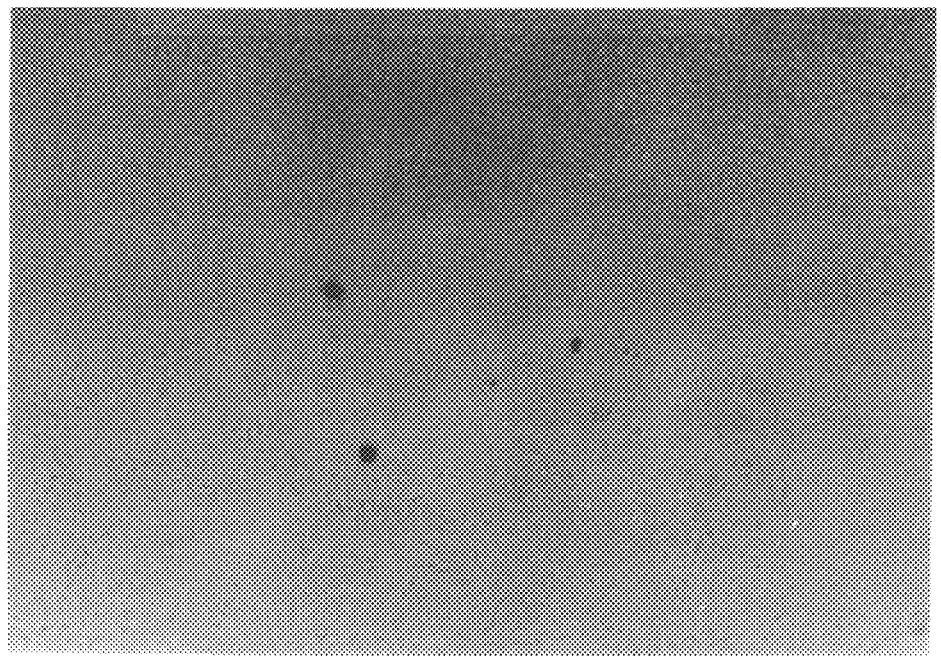
FIG. 3B

DEFECTIVE DNA VIRAL VECTOR COMPRISING A NEURAL TISSUE-SPECIFIC PROMOTER FOR IN VIVO EXPRESSION OF A GENE

CROSS-REFERENCE TO RELATED APPLICATIONS

The present application is a 371 of PCT/US93/07685, filed Aug. 16, 1993, which is a CIP of U.S. Ser. No. 07/930,875, filed Aug. 14, 1992, now abandoned, the disclosures of which are hereby incorporated by reference in their entireties. Applicant claims the benefits of these Applications under 35 U.S.C. §§ 120 and 371.

TECHNICAL FIELD OF THE INVENTION

The present invention relates to the field of neurobiology and, more particularly, to the diagnosis and treatment of various neural dysfunctions and disabilities by the direct introduction of genetic material. The invention further relates to the introduction of genetic material in somatic cells.

BACKGROUND OF THE INVENTION

The study of molecular neurobiology has developed with a view to implementing specific, effective therapeutic strategies to treat neural debilitation. Classically, three technical approaches have been followed to the present. The first, comprising the cloning and sequencing of novel cDNAs, seeks to develop specific genes that may be subsequently introduced in vivo to mediate and thereby achieve physiological alterations. The second strategy of molecular hybridization for the purpose of studying expression and regulation of specific messenger RNAs, likewise seeks to promote modifications through transcription. By contrast, the third strategy, involving direct manipulation of neuronal expression in vivo, seeks to actively alter neuronal cell physiology.

Two strategies that have been investigated in the direct approach involve the development of a transgenic vehicle, and efforts to deliver specific genes by incorporation within a viral vector that is delivered directly to the neuronal population of interest for in vivo expression. The former approach has been limited somewhat by corresponding limitation in the choice of species that are amenable to transgenic manipulations. Also, the transgenic approach has failed to provide the necessary specificity and selectively that is requisite for effective use. Tissue-specific promoters have been applied to this effect and have achieved some level of success [Forss-Petter et al. (1990) *NEURON.*, 5:187–197; Oberdick et al. (1990) *SCIENCE*, 248:223–226]. Even with this degree of selectively, however, expression in all cell types in which a given promoter is active is still unavoidable.

The use of viral constructs is the subject of extensive study, and particularly, with respect to the exploration of such a construct involving a defective herpes simplex viral vector based on a plasmid called an amplicon [Kaplitt et al. (1991) *MOL. CELL. NEUROSCI.*, 2:320–330; Spaete et al. (1982) *CELL*, 30:295–304; Geller et al. (1988) *SCIENCE*, 241:1667–1669]. Herpes simplex virus type 1 (HSV1) has been favored because of its broad host and tissue ranges. Several investigators including the present inventor have experimented with the incorporation into HSV1 vectors, and particularly defective viral vectors, various foreign genes for direct neuronal introduction in vivo. While such efforts have been pursued, and in particular, efforts with the lac Z gene of *E. coli* [Geller et al. supra], none of the vectors developed and used have ever resulted in stable expression, by which is meant expression in excess of two weeks of a gene introduced in a defective HSV vector.

Other investigators have pursued gene transfer in vivo by use of an HSV whole viral vector [see generally, Breakefield et al. (1991) *NEW BIOL.*, 3(3):203–218]. Successful genetic transfer in vivo has been achieved with these vectors [Dobson et al. (1990) *NEURON*, 5:353–360; Chiocca et al. (1990) *NEW BIOL.*, 2:739–746; Fink et al. (1992) *HUMAN GENE THER.*, 3:11–19]. While all of the noted investigators observed expression after introduction with the whole viral vector, expression ceased after two weeks in two instances and extended to five weeks and then ceased in the third [Dobson et al., supra]. In this latter connection, Dobson et al. noted that the lac Z gene was placed under the control of the viral promoter, and that the normal viral gene does not express during HSV latency, so that the cessation of expression after five weeks was attributed to cessation of promoter activity upon the entry of the viral DNA into a latent state.

As the potential value of stable and long-term expression of foreign genes in target neuronal populations and, particularly, in the brain, holds great promise for both diagnostic and therapeutic applications, it is clear that a need exists for the development of such a system and corresponding vector as will achieve such stable and long-term expression. It is to the achievement of this objective that the present invention is therefore directed.

The citation or identification of any reference in this application shall not be construed as an admission that such reference is available as prior art to the present invention.

SUMMARY OF THE INVENTION

In a first aspect of the present invention, a viral vector, preferably a defective viral vector, derived from a DNA virus has been prepared that is capable of the transfer and long-term in vivo expression of a gene in a somatic cell of a mammalian host. In particular, the vector of the invention is capable of the transfer and expression of a gene in neuronal cells and in endocrine cells. The vector of the invention contains a promoter that is endogenous to said host and that is derived from a gene normally expressed by said host. The gene contained in the vector can be foreign to the host, or it can be an autologous gene not normally expressed in that cell type, or for which the host is deficient.

In a specific example, the vector is a defective HSV1 vector which contains a preproenkephalin promoter, and specifically, a 2.7 kb fragment thereof associated with the lac Z gene of *E. coli*. The specific vector is named herein dvHENK, and the corresponding plasmid is named pHENK. The preparation of the vector of the present invention is described herein and depicted in FIG. 1, and the final plasmid is depicted in FIG. 2.

The invention correspondingly contemplates a recombinant DNA molecule comprising a DNA sequence encoding a molecule having demonstrated therapeutic effect on said host, the DNA sequence being disposed within a defective HSV vector containing a promoter that is endogenous to the host and that is derived from a gene normally expressed by the host.

The vector and recombinant molecules prepared in accordance with the present invention are believed to offer a significant opportunity for the development of gene therapy, particularly with organs where the cells involved do not normally divide. Accordingly, such organs as the brain and the spinal cord may be uniquely capable of treatment by gene therapy utilizing the present constructs. Additionally, endocrine cells are capable of producing molecules that demonstrate therapeutic activity encoded by a gene contained in the vectors of the invention.

Moreover, the vector of the present invention offers potential diagnostic utility, in that it can be used to create models of diseases such as Alzheimer's disease, for use in new drug discovery programs. A corresponding drug assay employing the present vector in such a model is likewise contemplated, and the invention accordingly extends to hosts transformed with the present vector.

The present invention extends further to methods for the treatment of neurodegenerative diseases such as Parkinson's disease and Alzheimer's disease, that have hitherto been resistant to conventional therapy, by the introduction of an effective amount of a therapeutically active gene directly into the debilitated neural cell by means of the direct introduction via the vector of the present invention. More particularly, adult brain tissue may be treated to correct neural dysfunctions or debilitations by the direct in vivo administration of an effective amount of a therapeutically active gene contained within the vector of the present invention.

Furthermore, a vector of the invention can be used for the treatment of a deficiency of a molecule found normally in the blood by transfecting endocrine cells with a gene encoding that molecule. Endocrine cells, which release hormones into the blood for rapid transport around the body, are ideally suited for the production and secretion into the blood stream of a molecule with therapeutic activity. Thus, a dysfunction associated with the deficiency of a particular molecule, e.g., a clotting factor or a hormone, can be treated by direct in vivo administration to cells of an endocrine organ of an effective amount of a therapeutically active gene contained within the vector of the present invention.

Corresponding compositions comprising therapeutically effective quantities of the present vector are likewise contemplated herein.

Accordingly, it is a principal object of the present invention to provide a vector for the long-term expression of a therapeutic gene by direct in vivo introduction into adult mammalian somatic cells, in particular neural tissue such as the brain and spinal chord, and endocrine tissue, such as the adrenal gland.

It is a further object of the present invention to provide a vector as aforesaid that remains active for a period of time sufficient to enable the therapeutic gene to integrate within the target neural tissue and to effect such therapies as result therefrom.

It is a still further object of the present invention to provide a model of neural disease or dysfunction by introduction of the vector of the present invention into a suitable test host or cellular colony.

It is a still further object of the present invention to provide a method for the in vivo direct treatment of neurodegenerative diseases such as Parkinson's disease and Alzheimer's disease, by introduction into neural cells of the vector of the present invention containing a gene encoding a therapeutically effective molecule for the treatment of such diseases as Parkinson's disease and Alzheimer's disease.

It is yet another object of the present invention to provide a method for the in vivo treatment of a deficiency of a molecule, such as a clotting factor or a hormone, by introduction into endocrine cells of the vector of the present invention containing a gene encoding the molecule for which there is a deficiency.

It is a still further object of the present invention to provide therapeutic compositions for such in vivo administration for the treatment of such diseases, comprising the vector of the present invention, additionally contained within a suitable carrier or medium where appropriate.

Other objects and advantages will become apparent to those skilled in the art from a review of the ensuing description which proceeds with reference to the following illustrative drawings.

BRIEF DESCRIPTION OF THE DRAWINGS

FIGS. 3 (A, B) comprises photomicrographs of sections of rat brain prepared and stained in accordance with X-Gal histochemical analysis, depicting by blue staining the presence of cells containing the vector of the present invention.

DETAILED DESCRIPTION

Figure 1:
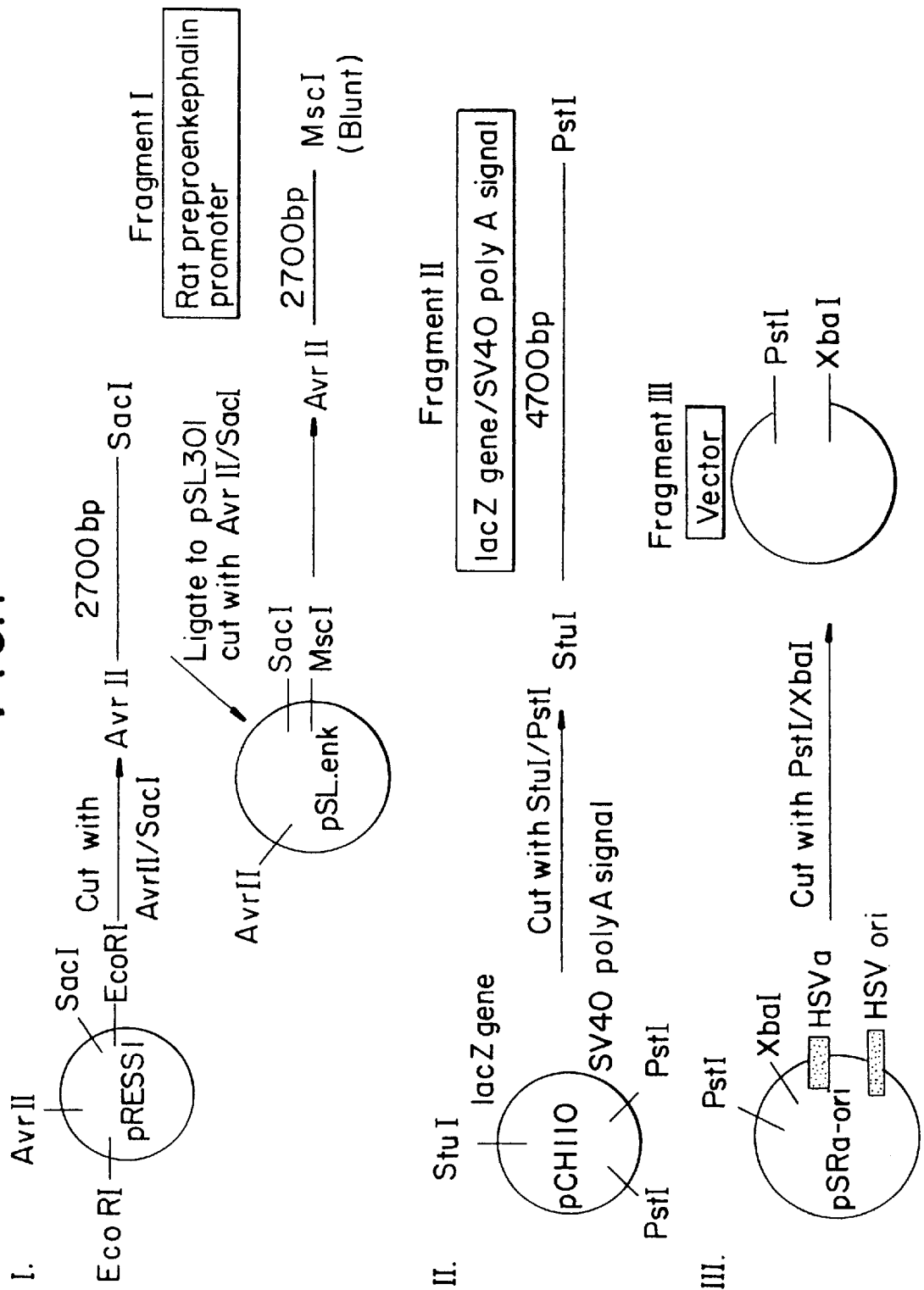
FIG. 1 is a chart depicting the procedure for the preparation and assembly of the vector of the present invention.
Figure 2:
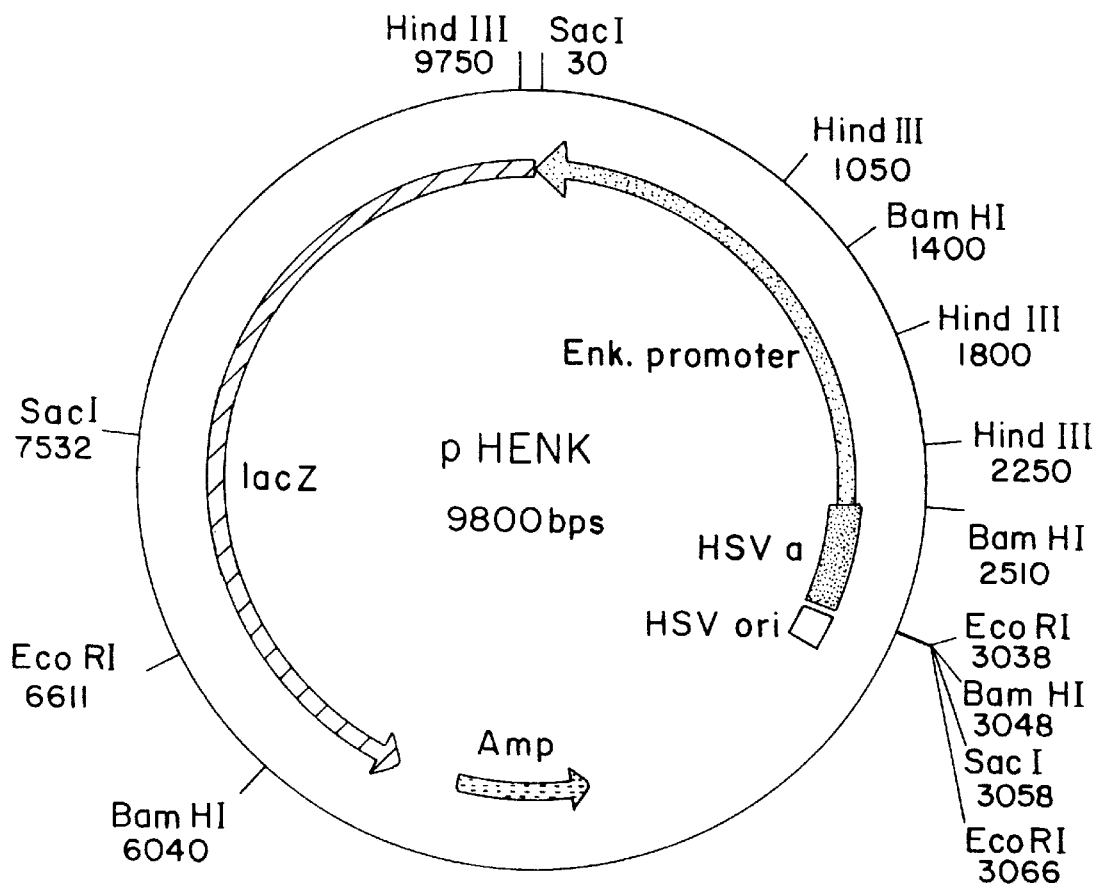
FIG. 2 is a restriction map diagram depicting the finally assembly vector of the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO 0 116 201, publication date Jan. 12, 1983; U.S. patent application Ser. No. 522,909, filed Aug. 12, 1983 now abandoned). Further, the alpha-factor leader and its analogs have been found to secrete heterologous proteins from a variety of yeast, such as Saccharomyces and Kluyveromyces, (EPO 88312306.9 filed Dec. 23, 1988; U.S. patent application Ser. No. 139,682, filed Dec. 30, 1987 now abandoned, and EPO Publication No. 0 301 669, publication date Feb. 1, 1989).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The term "therapeutic gene" is used herein to refer to a foreign or endogenous gene that expresses a molecule that has a therapeutic effect on the host. The endogenous gene can replace a mutant gene of the host that does not express a functional form of the molecule, or can supplement a host gene that does not express a sufficient amount of the molecule. The therapeutic effect can manifest in the transgenic cell, or locally in proximity to the transgenic cell. Alternatively, the therapeutic effect can manifest systemically or distally from the transgenic cell, as when an endocrine cell expresses a therapeutic gene introduced by a vector of the invention.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In its primary aspect, the present invention concerns a DNA viral vector containing a recombinant DNA molecule as defined herein that is useful for the long-term expression of a gene in adult somatic cells, in particular neural tissue, such as the brain and the spinal cord, and other organs where cells do not divide, such as endocrine tissue. More particularly, the invention comprises the development and application of a defective HSV vector, containing a gene that may have therapeutic activity when introduced into a particular target cell, with the gene under the control of a promoter, such as the preproenkephalin promoter, that is endogenous to the host and that is derived from a gene normally made by the host. Other animal transcriptional control regions, which exhibit tissue specificity and have been utilized in transgenic animals, can also be used to provide the endogenous promoter for use in the vectors of the invention: elastase I gene control region which is active in pancreatic acinar cells [Swift et al. (1984) CELL 38:639–646; Ornitz et al. (1986) COLD SPRING HARBOR SYMP. QUANT. BIOL. 50:399–409; MacDonald (1987) HEPATOLOGY 7:425–515]; insulin gene control region which is active in pancreatic beta cells [Hanahan (1985) NATURE 315:115–122], immunoglobulin gene control region which is active in lymphoid cells [Grosschedl et al. (1984) CELL 38:647–658; Adames et al. (1985) NATURE 318:533–538; Alexander et al. (1987) MOL. CELL. BIOL. 7:1436–1444], mouse mammary tumor virus control region which is active in testicular, breast, lymphoid and mast cells [Leder et al. (1986) CELL 45:485–495], albumin gene control region which is active in liver [Pinkert et al. (1987) GENES AND DEVEL. 1:268–276], alpha-fetoprotein gene control region which is active in liver [Krumlauf et al. (1985) MOL. CELL. BIOL. 5:1639–1648; Hammer et al. (1987) SCIENCE 235:53–58], alpha 1-antitrypsin gene control region which is active in the liver [Kelsey et al. (1987) GENES AND DEVEL. 1:161–171], beta-globin gene control region which is active in myeloid cells [Mogram et al. (1985) NATURE 315:338–340; Kollias et al. (1986) CELL 46:89–94), myelin basic protein gene control region which is active in oligodendrocyte cells in the brain [Readhead et al. (1987) CELL 48:703–712], myosin light chain-2 gene control region which is active in skeletal muscle [Sani (1985) NATURE 314:283–286], and gonadotropic releasing hormone gene control region which is active in the hypothalamus [Mason et al. (1986) SCIENCE 234:1372–1378].

In addition to defective HSV, other DNA viruses that can act as suitable vectors include, but are not limited to, attenuated or defective herpes simplex virus (HSV), papillomavirus, Epstein Barr virus (EPV), adenovirus, adeno-associated virus (AAV), and the like. Defective viruses, which entirely or almost entirely lack viral genes, are preferred.

Defective virus is not infective after introduction into a cell. Use of defective viral vectors allows for administration to cells in a specific, localized area, without concern that the vector can infect other cells. Thus, a particular locus, e.g., in the brain or spinal chord, or a specific endocrine gland, can be specifically targeted with the vector.

The particular vector that has been prepared and described in detail herein comprises defective HSV1 containing the *E. coli* lac Z gene and a promoter prepared from a DNA fragment of rat preproenkephalin gene taken 2.7 kb upstream from the transcriptional start site of the gene. The rat preproenkephalin gene is an opiate normally made in neurons of the brain and spinal cord, and is accordingly endogenous to the brain cells into which the vector was to be introduced. Preproenkephalin is also produced in certain endocrine tissue, in particular the adrenal glands. Thus, the recombinant gene contained in the exemplified vector is also expressed in adrenal gland cells, under control of the preproenkephalin promoter.

While not wishing to be bound to a particular theory of operation, it was speculated and borne out by the results presented herein that the inability of viral vectors prepared and tested in the past to achieve long-term expression derived from the choice of a viral promoter that became inactive when the virus entered latency, and that the choice of a promoter endogenous to the host cell would not susceptible to such dormancy. It is a particular discovery that the choice of a preproenkephalin promoter is not susceptible to this dormancy, whether expressed in neural cells or endocrine cells.

This particular solution was not clearly apparent however, as the inability to achieve long-term expression with neurons was considered to be equally as likely to be attributable to the following alternative hypotheses:

(1) Defective viral DNA is destroyed a short time after entering the nucleus. This was a strong possibility for the following reason. Normal HSV can enter a latent state, which is why infections persist throughout life. This latent state was observed by Dobson, et al., supra, when they showed five week expression in brain, since they saw 24 week expression in peripheral nerves. Latency is a poorly understood concept, and HSV encodes many viral genes. It is quite possible that latency requires HSV proteins or specific HSV sequences, and accordingly, that latency must be actively maintained. But, defective (amplicon) HSV DNA is not normal HSV DNA; it is mostly a plasmid with two small HSV sequences, and it encodes no viral gene products. The only gene expressed at all is the gene which is inserted, in this case lac Z. If latency requires some normal HSV function, then it is quite possible that defective HSV DNA would be degraded in the nucleus, since it lacks such things, and this would explain the short term expression.

(2) The neurons die after a short time. This is certainly a possibility with whole viral vectors, as suggested by Johnson, et. al. They found expression in cultured neurons for only a short period, and saw evidence of cytotoxicity, so they raised the possibility that the vector could kill the target cell, thereby limiting the length of observed expression. They also suggested possibilities included in hypothesis (1). While defective vectors should be less cytopathic, there was no evidence to the contrary, and accordingly, this theory was also a possibility.

The data presented herein demonstrates expression in the rat brain for 2 months using a defective HSV vector in which the lac Z gene is driven by the preproenkephalin promoter. In prior experiments performed by the present inventor employing a cytomegalovirus (CMV) promoter, cells expressing the lac Z marker gene were not visible even at 1 month. This demonstrates conclusively that hypotheses 1 and 2 were wrong, and that the promoter choice is an important factor.

The data presented herein also demonstrate expression in adrenal glands using a defective HSV vector in which the lac Z gene is driven by the preproenkephalin promoter.

As described earlier herein, the present invention offers significant diagnostic and therapeutic applications. The vector may be used to prepare particular animal disease models, for example of Parkinson's or Alzheimer's diseases, which may serve in drug discovery efforts. For example, a gene encoding amyloid precursor protein (APP) or the $\beta$-amyloid ($\beta$A) peptide can be introduced in the vector of the invention in a model for Alzheimer's disease.

Likewise, therapeutic protocols modeled after the methods disclosed hereinbelow may be developed to deliver particular therapeutically active genes to host cells in need thereof by means of the direct in vivo introduction of vectors prepared in accordance with the present invention. The ability to administer such gene therapy finds particular utility in the organs such as the brain where the cell population is adult. For example, as is readily appreciated by one of ordinary skill in the art from the foregoing description, a gene encoding human tyrosine hydroxylase, the enzyme involved in the production of L-dopamine (DOPA), can be introduced to increase the levels of the enzyme in cells of patients suffering from Parkinson's disease. Of particular interest in this regard is a gene encoding tyrosine hydroxylase under control of the pre-proenkephalin promoter, since enkephalin is endogenously expressed in the caudate nucleus, part of the basil ganglia, where lack of DOPA affects movement. Thus, the caudate nucleus, which is the target for the treatment of Parkinson's disease, endogenously expresses a gene under control of the preproenkephalin receptor. In another embodiment, a gene encoding a nerve growth factor (NGF), such as but not limited to NGF, ciliary neurotrophic factor, a neurotrophin, and the like, can be introduced in order to reverse the nerve degeneration associated with Alzheimer's disease. More particularly, the gene encoding an NGF can be under control of the preproenkephalin promoter for expression in the paraform cortex and the amygdala, which are particularly affected in Alzheimer's disease. The vectors of the invention can also be introduced into cells of the spinal chord. Of particular interest are genes encoding natural opiates, such as enkephalin, for expression under control of the preproen-kephalin promoter in cells of the spinal chord.

In yet a further embodiment, the gene introduced via a vector of the invention can encode a clotting factor, such as Factor VIII, which can be expressed and released into blood by endocrine cells. Alternatively, a gene encoding insulin can be introduced to endocrine cells for expression and release into blood. In particular, the gene introduced via the vector of the invention for expression in endocrine cells can be under the control of the preproenkephalin promoter, and expressed in adrenal glands.

Naturally, the invention may find utility in adaptation to other organs where similar strategies are possible, and the above is presented by way of illustration and not limitation.

The invention correspondingly contemplates compositions for administration in accordance with the afore-described methods, comprising appropriate unit doses of the present vector. Predetermined quantities of the vector may be prepared and administered as described, in accordance with appropriate protocols for such therapy. The exact quantities will vary with the particular therapy and are variable within the discretion of the skilled physician.

The present invention will be better understood from a review of the following illustrative description presenting the details of the constructs and procedures that were followed in its development and validation.

EXAMPLE 1

Materials and Methods pHENK was derived as follows:

Plasmid pPRESS1 (unrestricted gift of Dr. Steven Sabol) contained a 6.3 kb fragment of the upstream region of the rat preproenkephalin gene. To date, only 1,500 bp of this region have been sequenced (–1500 with respect to the transcriptional start site). By restriction mapping, an AvrII restriction site at –2700 bp was identified. A SacI site exists at +53 in the first untranslated exon of the rat preproenkephalin gene. Therefore, an approximately 2700 bp fragment of the promoter (–2700 to +53) was cloned out and placed into the AvrII/SacI sites of the "Superlinker" of plasmid pSL301 (Invitrogen) to create pSL.enk. pSL301 contains a unique MscI site downstream of the SacI site. MscI leaves a blunt end following digestion, and it was previously determined that MscI does not cut within the enkephalin promoter. In addition, there are no spurious ATG (translational start sites) between Sacd and MscI in this plasmid, so adverse influence on the expression of the desired enzyme was not anticipated.

Plasmid pHENK was then generated by ligation of the following three fragments.

i. 2700 bp MscI/AvrII fragment from pSL.enk, containing the rat preproenkephalin promoter.

ii. 4300 bp StuI/PstI fragment from plasmid pCH110 (Pharmacia), containing the bacterial lacZ gene and SV40 polyadenylation signal. Stu leaves blunt ends, and is therefore compatible with MscI.

iii. Vector pSRa-ori (see Kaplitt, et. al. (1991) *Mol. Cell. Neurosci.* 2:320–330), linearized With XbaI and PstI. Xba leaves a 5' overhang, which is compatible with AvrII.

Following cloning of plasmid pHENK, plasmid was grown in large quantities and purified on a CsCl gradient (Kaplitt, et. al.). Defective viral vector dvHENK was created by transfection of pHENK into rabbit skin cells, followed by superinfection as described previously (Kaplitt, et. al.). Viral stocks were propagated serially, and ratios of defective/helper virus was determined by dot blot analysis of viral DNA.

Virus was injected stereotaxically into rat brain as described (Kaplitt, et. al.). For long term expression, animals were maintained for 2 months. Animals were sacrificed and brains were fixed, removed, sectioned and processed for X-Gal histochemistry as described previously (Kaplitt, et. al.). Following coverslipping, positive cells were identified and photographed (FIG. 3).

For PCR analysis, coverslips were floated off positive sections and sections were rehydrated through decreasing alcohol. A region around positive cells was cut and removed with a 200 µl disposable pipette tip. Tissue was placed in a 0.6 ml tube containing 10 µl of digestion solution. Digestion solution consisted of 1×PCR buffer (Cetus)/200 µg/ml proteinase K (Sigma)/%0.5 Tween-20 (Sigma). Tissue was digested for 30 min. at 65° C., and protease was inactivated by heating 20 min. at 85° C.

Samples were cooled and then additional solution was added for PCR to final volume of 100 µl. The final 100 µl PCR reaction contained: 100 pmol lacZ Primer I/100 pmol lacZ Primer 2/1×PCR buffer/200 mM of each of dATP, dCTP, dTrP, dGTP/2.5 Units Taq polymerase (Cetus). PCR reactions were performed in a GeneAmp thermal cycler (PerkinElmer). The following reaction was performed: 1 cycle of 1 min. @94° C./1 min. @65° C./1 min. @72° C. This was followed by 39 cycles of 45 sec. @94° C./45 sec. @65° C./30 sec. @72° C. Following the first reaction, 1 µl of product was removed and diluted 1:100. One µl of diluted product was placed into a new reaction. This contained the same components as the first, with the exception that the primers were replaced with new primers internal to the first set ("nested" PCR). This confirms specificity, as non-specific products from the first reaction should not amplify with a second set of specific, internal primers. The conditions for the second reaction were 20 cycles of 45 sec. @94° C./45 sec. @65° C./30 sec. @72° C. Products were analyzed by electrophoresis on a 1.5% agarose gel. Bands were visualized under an ultraviolet lamp by ethidium bromide staining.

RESULTS

Figure 4:
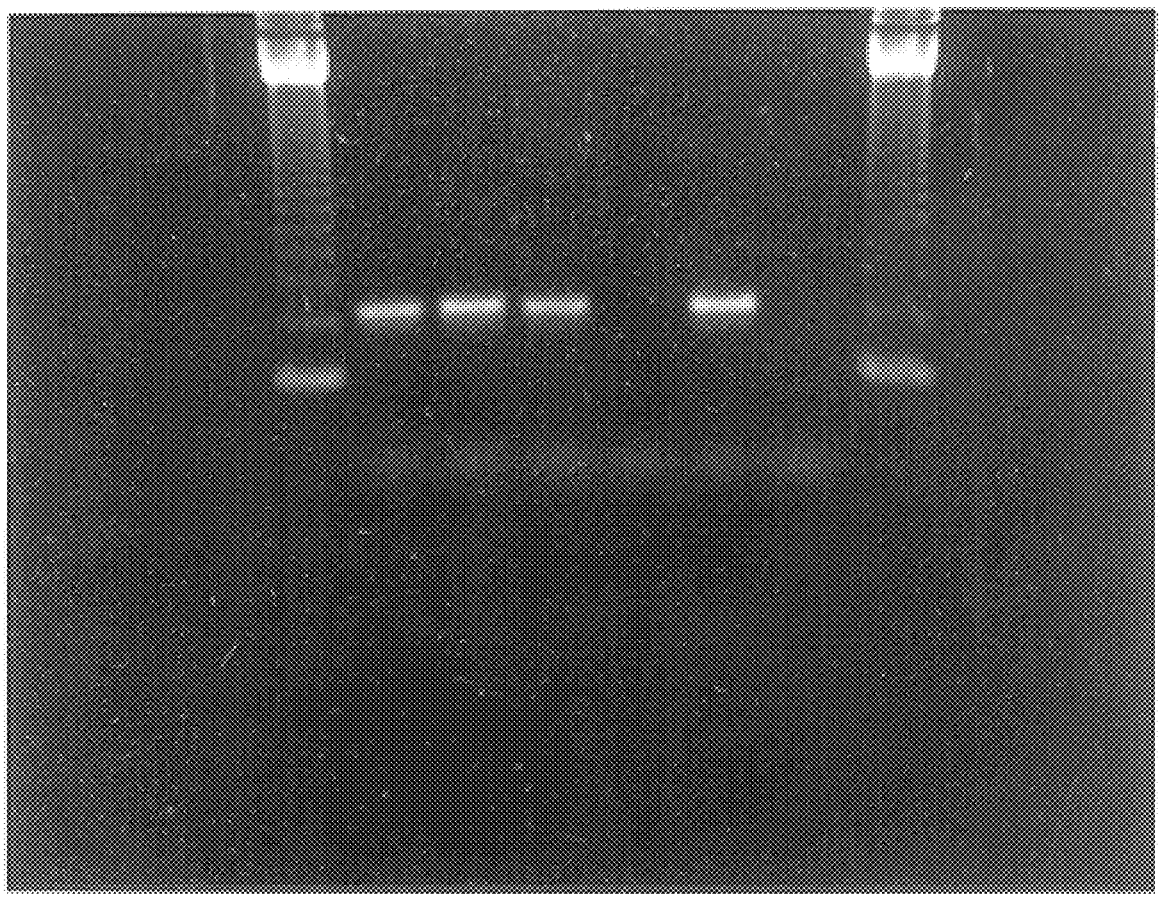
FIG. 4 is a photograph depicting the results of DNA gel electrophoresis.

Referring to FIG. 4, the lanes for the DNA gel are as follows (from left to right):
1. Marker (123 bp ladder; each band is 123 bp apart)
2. Positive region 1—contained 3 blue (positive) cells
3. Positive region 2—contained 10 blue cells
4. Positive region 3—contained 2 blue cells
5. Uninjected, negative control brain region—no blue cells
6. Positive control—pHENK plasmid DNA
7. Negative control—Blank (no DNA)
8. Marker (same as 1)

Referring to FIG. 4, all three positive regions from X-Gal staining confirmed that pHENK DNA was still present after 2 months, while in a negative, uninjected region and as expected, no PCR product was detected. The positive and additional negative control were also as expected. A 269 bp band was produced, which was the size predicted from the position of the PCR primers on the sequence. Thus, this gel confirms that there is viral DNA present in positive regions after 2 months, and supports the conclusion that blue cells do in fact represent positive cells.

DISCUSSION

Previously it has been demonstrated that an amplicon-based herpes simplex virus type 1 (HSV1) defective viral vector can result in successful transfer and expression in vivo of the bacterial lac Z gene in the adult rat brain (Kaplitt, et. al. (1991) *Mol. Cell. Neurosci.* 2:320–330). To date, there has been no report of in vivo expression beyond 2 weeks using any HSV1 vector.

As stated above, a 2.7 kb DNA fragment from the rat preproenkephalin (PPE) upstream region was used in the vector to drive expression of the lac Z gene. Expression was detected both 3 days (short-term) and 2 months (long-term) post-injection. In contrast, when the lac Z gene was driven by the human cytomegalovirus (CMV) immediate-early promoter, positive cells were not observed beyond two weeks following injection. There were no behavioral abnormalities in animals with 2 month expression, and brain sections showed no evidence of pathology. Regional analysis demonstrated strong expression from the 2.7 kb PPE fragment in the caudate nucleus and amygdala plus positive cells in ventromedial hypothalamus (VMH), all regions with high endogenous PPE mRNA levels. Limited, occasional expression was observed in regions which do not have high endogenous PPE mRNA levels.

The above results demonstrate that HSV defective viral vectors prepared in accordance with the present invention represent a novel alternative to transgenic mice for analysis of neuronal promoter function in vivo, and suggests that such vectors might be useful for long-term modification of neuronal function in human patients. More generally, the preparation of vectors in the present fashion offers the opportunity to develop a broad range of therapeutic strategies involving direct genetic intervention that will yield prompt and highly predictable results and benefit.

EXAMPLE 2

The present example relates to expression of a lac Z gene in rat adrenal cells. The defective HSV-1 vector utilizing the preproenkephalin promoter described in Example 1 was used without further modification. An incision was made in the abdomen below and slightly dorsal to the costophrenic angle. The adrenal gland was exposed in its retroperitoneal position. A Hamilton syringe was used to draw 5–10 µl of dvHENK, the HSV-1 vector containing the pHENK plasmid, stock (containing either $1.6 \times 10^5$ defectives/ml or $5.7 \times 10^6$ defectives/ml) into a 30-gauge stainless steel injection needle. The virus was injected directly into the substance of the adrenal gland as described [Kaplitt et al. (1990) *MOL. CELL. NEUROSCI.*, 2:320–330). After injection of the vector, the animal was sewn up and allowed to recover. Three days later, the animal was sacrificed. The adrenal glands were recovered and tissues prepared and stained as described in Example 1.

Figure 5:
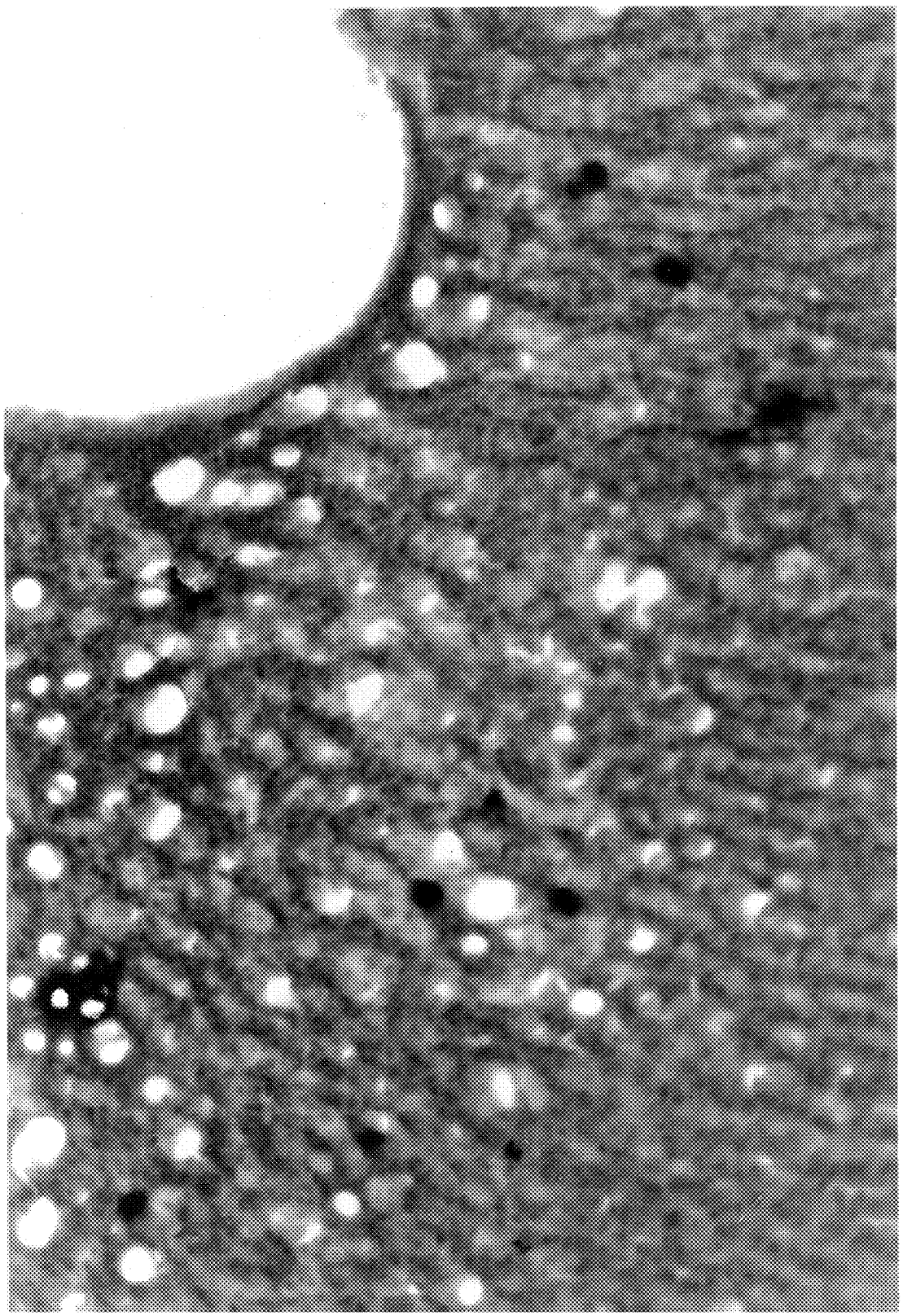
FIG. 5 is a photomicrograph of a section of rat adrenal gland prepared and stained in accordance with X-Gal histochemical analysis, depicting by blue staining the presence of adrenal cells containing the vector of the present invention.

FIG. 5, which is a photomicrograph of the adrenal cells stained blue after the X-Gal histochemistry, demonstrates expression of the gene introduced by the vector under control of the preproenkephalin promoter.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A replication defective DNA viral vector for the in vivo expression of a gene of interest in a mammalian host cell, wherein said vector comprises the gene of interest in operable linkage with a neural tissue-specific promoter such that said gene of interest is expressed in said host cell, wherein said neural tissue-specific promoter is a promoter of a gene encoding a protein normally produced by said host cell, and wherein said defective DNA viral vector entirely or almost entirely lacks viral genes.

2. The vector of claim 1, wherein said host cell is either a neural tissue cell or an endocrine cell.

3. The vector of claim 2, wherein said neural tissue cell is a brain cell.

4. The vector of claim 1, wherein said promoter is a promoter of the preproenkephalin gene.

5. The vector of claim 1, wherein the gene of interest encodes a product selected from the group consisting of amyloid precursor protein, β-amyloid peptide, and tyrosine hydroxylase.

6. The vector of claim 1, wherein said vector is a defective Herpes Simplex Virus-1 (HSV-1) vector which comprises the lac Z gene of *E. coli* operably linked to a promoter of the preproenkephalin gene.

7. The vector of claim 6, wherein said promoter is a 2.7 kb fragment of said preproenkephalin gene.

8. The vector of claim 1, wherein said vector comprises the plasmid pHENK.

9. A replication defective DNA viral vector comprising a DNA sequence encoding a product having a demonstrated therapeutic effect on a mammalian host cell, wherein said DNA sequence is operably linked to a neural tissue-specific promoter such that said DNA sequence is expressed in said host cell, wherein said promoter is a promoter of a gene encoding a protein normally produced by said host cell, and wherein said defective DNA viral vector entirely or almost entirely lacks viral genes.

10. The vector of claim 1, which is selected from the group consisting of a Herpes Simplex Virus (HSV) vector, a Papillomavirus vector, an Epstein Barr Virus (EBV) vector, an Adenovirus vector, and an Adeno-Associated Virus (AAV) vector.

11. The vector of claim 10, which is an HSV vector.

12. The vector of claim 10, which is an AAV vector.

13. A replication defective DNA viral vector for the in vivo expression of a gene of interest in a mammalian host cell, wherein said vector comprises the gene of interest in operable linkage with a neural tissue-specific promoter such that said gene of interest is expressed in said host cell for at least two months, wherein said neural tissue-specific promoter is a promoter of a gene encoding a protein normally produced by said host cell, and wherein said defective DNA viral vector entirely or almost entirely lacks viral genes.

14. The vector of claim 13, wherein said mammalian host cell is either a neural tissue cell or an endocrine cell.

15. The vector of claim 14, wherein said neural tissue cell is a brain cell.

16. The vector of claim 13, which is selected from the group consisting of a Herpes Simplex Virus (HSV) vector, a Papillomavirus vector, an Epstein Barr Virus (EBV) vector, an Adenovirus vector, and an Adeno-Associated Virus (AAV) vector.

17. The vector of claim 16, which is an HSV vector.

18. The vector of claim 16, which is an AAV vector.

19. The vector of claim 1, wherein the gene of interest encodes a clotting factor or a hormone.

20. The vector of claim 2, wherein said neural tissue cell is a spinal chord cell.

21. The vector of claim 14, wherein said neural tissue cell is a spinal chord cell.

* * * * *